United States Patent [19]

Poler

[11] 4,402,579
[45] Sep. 6, 1983

[54] CONTACT-LENS CONSTRUCTION

[75] Inventor: Stanley Poler, New York, N.Y.

[73] Assignee: Lynell Medical Technology Inc., New York, N.Y.

[21] Appl. No.: 288,217

[22] Filed: Jul. 29, 1981

[51] Int. Cl.³ .................... G02C 7/04; A61F 1/16
[52] U.S. Cl. ...................... 351/160 R; 3/13
[58] Field of Search ............. 3/13; 351/160 R, 160 H, 351/161, 159

[56] References Cited

U.S. PATENT DOCUMENTS

| | | | |
|---|---|---|---|
| 2,117,770 | 5/1938 | Row | 351/160 R |
| 2,644,985 | 7/1953 | Crandon | 351/160 R X |
| 4,080,709 | 3/1978 | Poler | 3/13 X |
| 4,126,904 | 11/1978 | Shepard | 3/13 |
| 4,149,279 | 4/1979 | Poler | 3/13 |
| 4,158,030 | 6/1979 | Stoyan | 3/13 X |
| 4,206,518 | 6/1980 | Jardon et al. | 3/13 |
| 4,242,762 | 1/1981 | Tennant | 3/13 |
| 4,253,199 | 3/1981 | Banko | 3/13 |

FOREIGN PATENT DOCUMENTS

| | | | |
|---|---|---|---|
| 2151028 | 4/1972 | Fed. Rep. of Germany ... | 351/160 R |
| 2717706 | 10/1978 | Fed. Rep. of Germany ............ | 3/13 |
| 563174 | 7/1977 | U.S.S.R. .................................. | 3/13 |

*Primary Examiner*—Ronald L. Frinks
*Attorney, Agent, or Firm*—Hopgood, Calimafde, Kalil, Blaustein & Judlowe

[57] ABSTRACT

The invention contemplates integral lens-and-haptic structure and a technique of making the same, using sheet material as the only ingredient of the ultimate product, which may be an intraocular implant or for extraocular (i.e., cornea-contact) application. The sheet material is of substantially the ultimate thickness of the lens, and may be of optical-quality glass or of a transparent plastic which is inert to body fluids. Suitably coordinated masking and etching steps determine the contour of the ultimate central circular lens as well as the thickness and fenestration detail of the ultimate thin flexible haptic formations which are integral with and extend radially outward of the lens blank. Lens-surface curvature may be developed before or after haptic formation.

11 Claims, 20 Drawing Figures

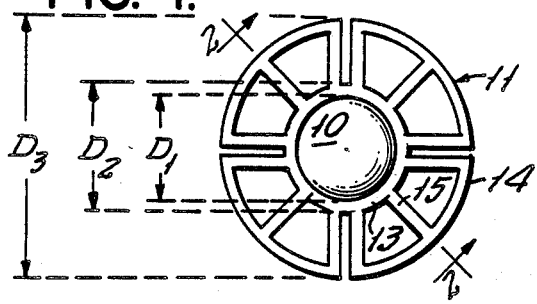
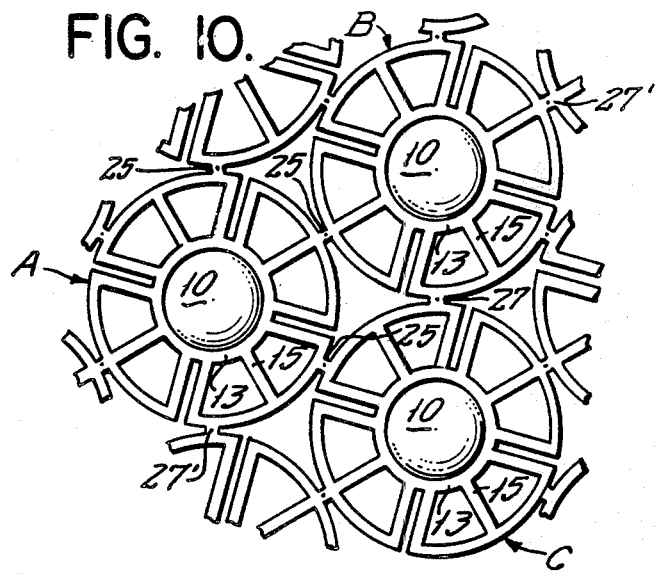
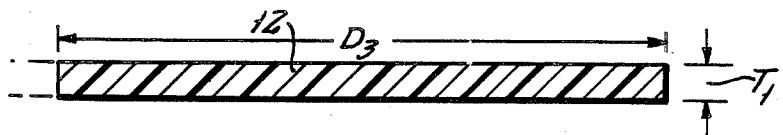
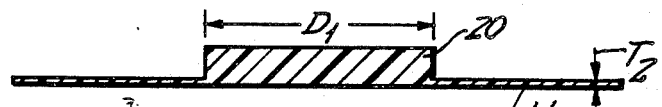
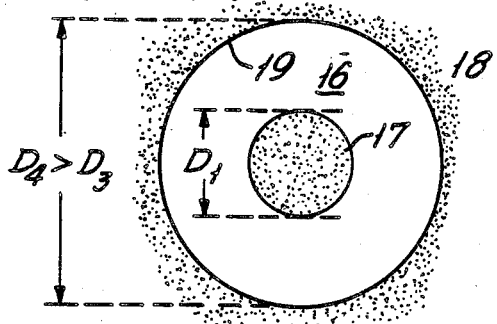
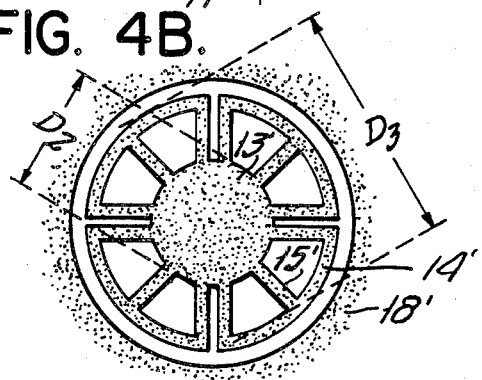
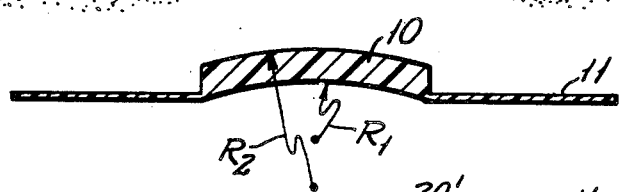
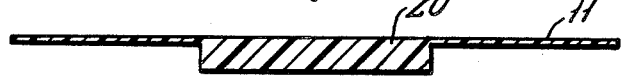
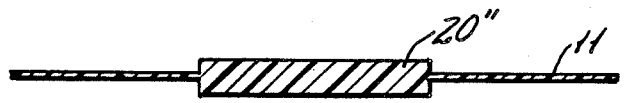
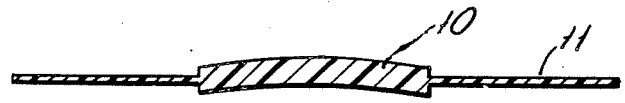

CONTACT-LENS CONSTRUCTION

BACKGROUND OF THE INVENTION

This invention relates to lens and haptic structures having application as intraocular lens implants, or as extraocular devices for contact application to the cornea, for wear in place of spectacles.

As intraocular devices, such structures and methods of making the same as illustratively treated in my U.S. Pat. No. 4,080,709, and as extraocular devices, such structures are illustratively treated in my copending application, Ser. No. 124,941, filed Feb. 26, 1980.

Design philosophy behind intraocular and extraocular devices of the character indicated holds that the lens element shall be an optically finished unitary part, and that associated haptic structure shall be a separate thin flexible part or parts devised for central support of the lens element and for suitably compatible stabilized referencing engagement with adjacent body features.

There is another category of intraocular lens, exemplified by Choyce, et al., U.S. Pat. No. 4,087,866, wherein lens and haptic structure are the integral product of plastic-molding. But such products do not lend themselves to fabrication with glass, nor to known glass-lens finishing techniques. Moreover, injection-molded plastic materials are inherently incapable of providing the optical quality and uniformity that is available from certain plastic materials which are available in flat-sheet form.

BRIEF STATEMENT OF THE INVENTION

It is an object to provide improved integrally formed lens and haptic structures of the character indicated.

Another object is to provide methods of manufacture of such structures which are inherently applicable to fabrication from glass or from a plastic, as the starting and the only material of the ultimate product.

A specific object is to meet the above object with structures and techniques which utilize flat sheet material as the starting and only material of the ultimate product.

The invention achieves these objects and certain further features by employing suitably coordinated masking and etching steps to determine the peripheral contour of the ultimate central lens as well as the thickness and fenestration detail of the ultimate thin flexible haptic formations which are integral with and extend radially outward of the lens blank. In all cases, the starting material is flat sheet stock, of thickness to provide for the overall ultimate axial extent of the lens. Lens-surface curvature may be developed prior to but is preferably developed after haptic formation. The masking and fenestration detail are provided via photo-etch techniques and are applicable to mass production of plural duplicates of the identical lens-and-haptic structures from a single sheet through formative operations performed concurrently and in common on all structures of a given sheet.

DETAILED DESCRIPTION

Illustrative structures and techniques of the invention will be described in detail in conjunction with the accompanying drawings, in which:

FIG. 1 is a plan view of a single-piece integrally formed lens and haptic construction of the invention;

FIG. 2 is a sectional view, taken at 2—2 in FIG. 1;

FIG. 3 is an enlarged schematic sectional representation of sheet starting material, for the aspect depicted in FIG. 2, i.e., what begins as shown in FIG. 3 ultimately becomes what is shown in FIG. 2;

FIG. 4 is a diagram similar to FIG. 3, to show the result of an intermediate step in proceeding from the material of FIG. 3 to the product of FIG. 2;

FIGS. 4A and 4B are diagrammatic representations of different masks used to create the intermediate stage of FIG. 4;

FIG. 5 is a view similar to FIG. 4, to illustrate a finishing step, for the product of FIGS. 1 and 2;

FIGS. 6 and 7 are views similar and respectively corresponding to FIGS. 4 and 5, to illustrate a modification;

FIGS. 8 and 9 are views similar and respectively corresponding to FIGS. 6 and 7, to illustrate a further modification;

FIGS. 10 and 11 are similar fragmentary plan views of two alternative multiple-structure layouts on a single sheet of starting material, for mass-production purposes;

Figure 11:
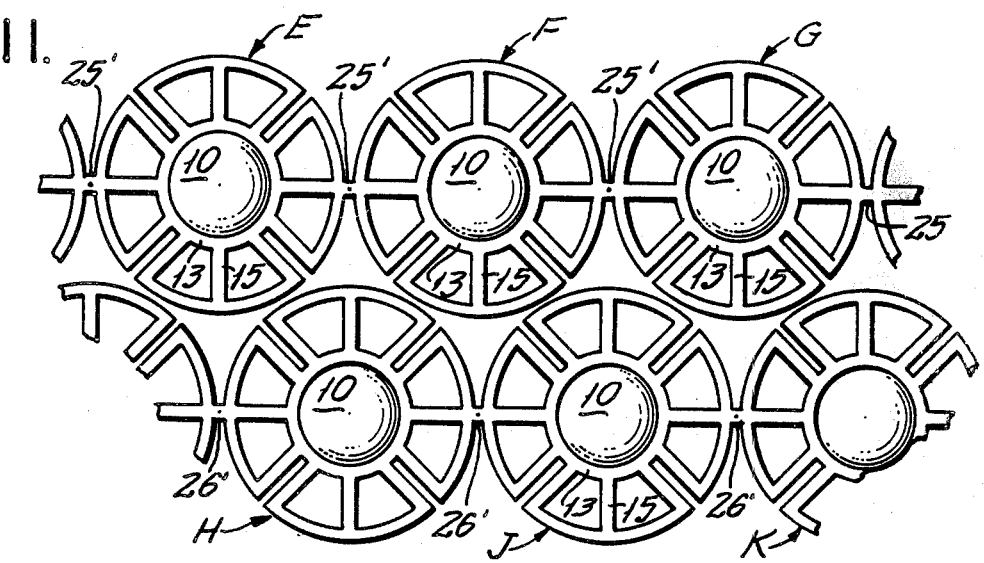

In the form of FIGS. 1 and 2, the invention is shown in application to an extraocular or contact-lens assembly, strongly resembling multiple-component structure as disclosed in my said copending application, Ser. No. 124,941, but in reality comprising a central lens 10 and haptic structure 11 which are integral with each other, being the product of selectively etched reduction from starting material in the form of flat sheet stock 12, of thickness $T_1$, as shown in FIG. 3. As will later appear, the sheet stock 12 may be suitable plastic or glass, and inert to body fluids. For convenience, dimensional symbols have been applied to identify: lens diameter at $D_1$, which may be in the range of 6 to 9 mm; an inner circumferential haptic band or ledge 13, which is preferably at least 0.25-mm wide, to account for its outer diameter $D_2$ in the range of 6.5 to 9.5 mm; and haptic outer diameter $D_3$ which may be in the range up to 20 mm, and thus in excess of the 12 to 14 mm diameter of the iris of an eye. It will be understood that haptic 11 may be characterized by very substantial fenestration, meaning that the structure is primarily "open", for normal air or "breathing" exposure of the surface of the cornea to which it is applied. Such substantial fenestration is shown and described in said copending application Ser. No. 124,941, and is therefore not repeated here. It suffices to note that the detail of fenestration and the varieties of haptic configuration of said copending application are achievable for the techniques and structures to be described herein; therefore, such detail is not here repeated. It is also to be noted that the detail of haptic configuration and size, for intraocular-lens application, including lens size and power appropriate to intraocular use, may be achieved with the invention, so that dimensions and shapes given herein for the extraocular situation are to be regarded as merely illustrative and not limiting.

Further, and more specifically, for the contact-lens situation and as described in detail in said application Ser. No. 124,941, the haptic structure 11 is normally flat but so thin and of such axially compliant nature as to be self-conforming to the curvature of the cornea and to adhere thereto via surface moisture on the cornea.

It suffices here to describe the haptic 11 as comprising four arcuate feet 14, connected to each other and to lens element 10 only via integral radial legs 15 to ledge 13. Lens thickness $T_1$ is generally in the range 0.001 to 0.007 inch, for extraocular applications, and in the range of 0.002 to 0.020 for intraocular applications; and haptic thickness $T_2$ (FIG. 4) is in the order of 0.001 to 0.003 inch for both applications.

To proceed from the sheet 12 of FIG. 3 to the intermediate stage of FIG. 4, I utilize mask and photo-etch techniques which are illustratively described in my U.S. Pat. No. 4,080,709 and which therefore need not be repeated here. It suffices to indicate that for present purposes, a mask as in FIG. 4A is used for the chemical or other etching of the upper surface of sheet 12, and that a different mask as in FIG. 4B is used for such etching of the lower surface of sheet 12. These two different etchings may proceed concurrently, but I prefer to perform each operation separately, thereby achieving full control of the particular depth of erosion desired from each side of sheet 12.

More specifically, the mask of FIG. 4A may be a precise photographic reduction from a master drawing, the reduction being to expose a photosensitive coating of the upper surface of sheet 12, the exposed coating being thereafter developed to leave a deposited opaque masking pattern on the sheet. Since it is my preference to first etch from one side and then from the other, I fully expose the photosensitive coating on the lower surface of sheet 12, so that upon development, the lower surface is entirely opaque and is thus incapable of permitting an etch from the lower side. With the thus-masked sheet then exposed to an etching environment, only the areas not opaquely masked will be etched, and this first etching is timed for penetration to the depth $T_1 - T_2$, thus leaving only haptic thickness $T_2$ in the etched region. As seen in FIG. 4A, this first mask is characterized for etching exposure of the circular annulus 16, defined internally by a lens-size opaque circular area 17 of diameter $D_1$ and on the outside by a circumferentially enveloping opaque area 18. The outer opaque area 18 has a circular inner edge 19 of diameter $D_4$ slightly greater than ultimate haptic diameter $D_3$.

Having etched through the mask of FIG. 4A to the depth $T_1 - T_2$, all maskings are stripped and the specimen recoated with photosensitive material. The mask pattern of FIG. 4B is then exposed and developed on the underside of the specimen, in precise concentric relation with the FIG. 4A exposure and etching, while the upper surfaces of the central lens-blank region 20 and surrounding annular haptic area 11 are totally exposed and developed to render etching exposure only through the FIG. 4B mask on the lower surface of the specimen. This second etching is allowed to proceed fully through the ultimate haptic thickness $T_2$, at which time the intermediate product of FIG. 4 becomes severed from surrounding original sheet material. It is, of course, possible then to strip maskings from the specimen and to proceed thence with lens-finishing. However, it is my preference that the mask of FIG. 4B be formed with at least one later-severable tie-forming opaque connection between the fenestration-defining inner pattern (within diameter $D_3$) and the surrounding opaque pattern 18', corresponding to surrounding mask material at 18 in FIG. 4A.

The inner pattern of the mask of FIG. 4B, i.e., within the inner circular edge of surrounding opaque material 18', will be seen to have the haptic-fenestration detail described in connection with FIG. 1, and therefore in FIG. 4B corresponding inner opaque parts of this mask are given FIG. 1 reference numbers, with primed notation. However, in the mask of FIG. 4B, the full area 13' within the outer confines of ledge 13, i.e., within the circle of diameter $D_2$ is opaque, to avoid etching the lens blank region 20.

Having performed the second etch to the pattern of FIG. 4B, all mask deposits are stripped from the partially completed specimen, to permit lens-finishing. In the individually separated specimen situation, each item must be separately handled, but in the edge-interconnected situation, the individual specimens may be more readily handled by mass lens-finishing techniques. One pattern of edge-interconnected specimens is illustrated in FIG. 10, wherein each partially completed specimen (per FIG. 4) is in nested adjacency to and interconnected with six surrounding like specimens; in the fragmentary showing of FIG. 10, three thus-nested partially completed specimens A-B-C are connected, as by a severable tie 25 between specimens A and B, by a severable tie 26 between specimens A and C, and by a severable tie 27 between specimens B and C.

FIG. 11 is a diagram similar to FIG. 10, but showing a different pattern of severable interconnection of partially completed specimens, also lending itself to mass-production handling in lens-finishing phases of production, as will later become more clear. In FIG. 11, the pattern of severable interconnection is on discrete parallel alignments of connection. For example, the partially completed specimens E-F-G of one such alignment are severably interconnected at 25' to each other, and the partially completed specimens H-J-K of the next adjacent such alignment are severably interconnected (at 26') but are not connected to the specimens of alignment A-B-C or to those of any other alignment. In other words, the arrangement of FIG. 11 permits automated handling of linear arrays of severably connected specimens.

Returning now to the matter of lens-finishing, and taking the case of having performed etching steps on a starting sheet of suitable plastic, the partially completed specimen of FIG. 4 is first accurately positioned in a forming die. Then, the lens shape which may involve an inner concave surface of radius $R_1$ and an outer convex surface of different radius $R_2$, is established by plastic deformation under elevated compressional pressure within the die, resulting in a finished product, as shown in FIG. 5. In this particular finished product, it will be noted that the convex anterior surface of lens 10 is offset from the ledge 13 of integral haptic 11 connection, and that the posterior surface of lens 10 is effectively flush with the haptic.

FIGS. 6 and 7 illustrate a modification wherein the etching to form the haptic 11 uses masks as in FIGS. 4A and 4B in the reverse orientation from that described for FIG. 4, in order to produce haptic connection with the lens blank 20' at the anterior region, and at axial offset from the posterior surface of the lens blank. In other words, the first or step-edging procedure to the mask pattern of FIG. 4A may be developed in reference to the lower (potentially posterior) surface of the starting sheet 12, while the haptic-detail etching attributable to the mask pattern of FIG. 4B may be developed in reference to the upper (potentially anterior) surface of sheet 12. Lens curvatures may be developed as previously described, resulting in FIG. 7 in a plane anterior surface of the lens 10 and a concave posterior surface. It goes without saying that if permanent curvature is desired in either of the lens and haptic configurations of FIGS. 5 and 7, such haptic curvatures may be the product of the same compressional die procedure as induces lens curvatures.

FIGS. 8 and 9 illustrate that described masks and etching may also be used to produce an integral lens and haptic configuration wherein the haptic 11 integrally joins the lens-blank region 20″ at axial offset from both the anterior and the posterior surfaces of the lens. To produce this configuration, the first etching step is performed on a blank sheet 12 which has had mask deposits to the pattern of FIG. 4A, applied in axial register to both sides of the sheet. Etching is timed to achieve haptic thickness $T_2$, but since etching proceeds simultaneously against identical FIG. 4A masks on both sides of sheet 12, the etch time will be one-half that required for first etching in the FIG. 4 and FIG. 6 situations. Second etching, to the pattern of FIG. 4B may be as described for either of the FIG. 4 or FIG. 6 situations, as will be understood.

Figure 12:
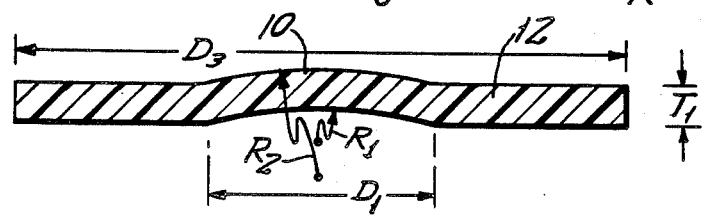
FIGS. 12 and 13 are sectional views to the scale of FIGS. 3, 4 and 5, to illustrate a modified technique.
Figure 13:

Thus far, all procedures have involved mask and etch techniques first, followed thereafter by lens-finishing steps. But FIG. 12 illustrates that this is not necessarily to be considered a limiting sequence. In FIG. 1, the lens-defining steps are first performed on the starting sheet 12, the particular lens shown being recognizable as that of FIG. 5. Thereafter, it will be understood that any of the various mask-and-etch sequences described for FIGS. 4, 6 and 8 may be used, depending on the desired ultimate axial location of integral haptic connection to the lens 10. For illustration, FIG. 13 shows the product configuration of FIG. 5 resulting from mask-and-etch sequences of FIG. 4, applied to the pre-formed lens 10 of FIG. 12.

Also thus far, all procedures and configurations have been described with a tacit assumption that the starting material is a plastic sheet 12. But this need not be the case, in that the sheet 12 may be of optical-quality glass, with etching techniques performed as appropriate for glass, in the context of masks (e.g., to to FIGS. 4A and 4B patterns) of nature appropriate to the etching technique. Nor is compressional-die deformation of the sheet material 12 to be limited to plastics, in that upon application of heat to induce softening, the pressed deformation of glass lens-blank regions of integral lens-and-haptic structures consisting entirely of the same piece of glass are feasible.

It is, however, my preference that recognized optical-finishing techniques be employed in the finishing of integral lens-and-haptic configurations which are made of glass. And FIGS. 14, 15 and 16 illustrate this preference.

Figure 14:
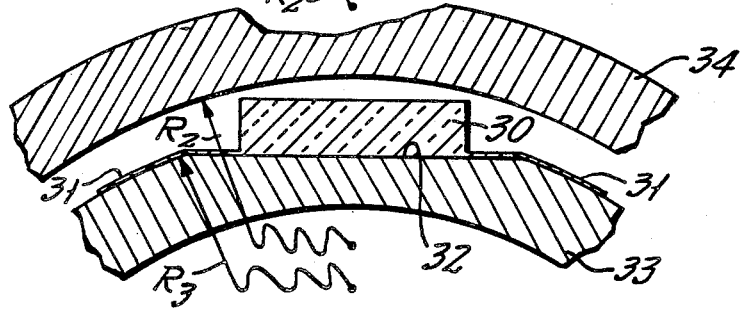
FIGS. 14 and 15 are sectional views, to the scale of FIGS. 4 and 5, to illustrate successive finishing steps for simultaneously finishing the convex surface of each of a plurality of lens elements of optical glass.

In FIG. 14, a partially completed all-glass specimen comprises a central lens blank 30 with integral haptic features 31 which are sufficiently thin to be axially compliant. The flat blank region 30 is mounted to a suitable flat platform location 32 of a conventional generally truncated spherical multiple-blank support 33, being removably affixed thereto by wax embedment in accordance with accepted practice, and wax being also used to removably retain the flexible haptic portions 31 in conformance to curved surfaces of support 33, adjacent the platform locations 32. The curvature of radius $R_3$ to which haptic features 31 are thus temporarily conformed is less than or at least relieved from the locus of ultimate convex grinding curvature $R_2$ to which the anterior surface of blank 30 is to be ground. For such grinding, a master grinding member 34 having a concave master-grind curvature of radius $R_2$ is shown poised at offset from blank 30 and its support 33, in readiness to commence conventional grinding of the convex anterior lens surface, to radius $R_2$.

It should be noted that support 33 may include flat platforms 32 at spacings and alignments appropriate to the multiple mounting of severably connected partially completed all-glass specimens, for example, a longitudinally connected array as described in connection with FIG. 11. In that event, each of the lens blanks (30) of the connected array will have its own flat platform (32) and all blanks and their haptics will be removably fixed by wax, in position for grinding in unison against master grinding member 34, all to the same convex curvature $R_2$. Each resulting integral lens-and-haptic product, after grinding against master 34, will then have the unit appearance depicted in FIG. 15, with a plano-convex lens 30′, once the wax connection is dislodged by heat.

Figure 15:
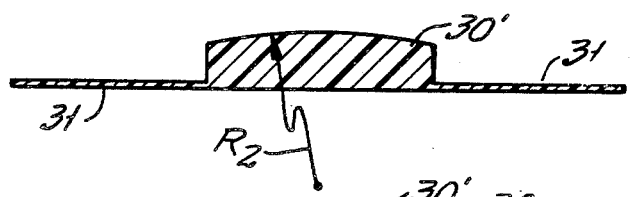
Figure 16:
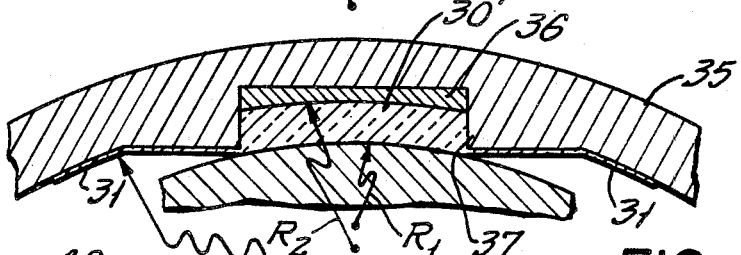
FIG. 16 is a diagram similar to FIG. 14, to show a set-up for simultaneously finishing the concave surface of each of a plurality of lens elements of optical glass.

FIG. 16 illustrates that conventional glass-lens finishing techniques are also applicable to the generation of concave surfaces, as to radius $R_1$ on the posterior surface of the structure of FIG. 15. To this end, a support member 35 has a concave surface which may be generally spherical to larger radius $R_4$ than (or at offset from) the locus of the $R_1$ concave surface to be ultimately ground, and this surface is characterized by local recesses or pockets 36 of circular configuration to locate the periphery of partially ground lens blank 30′ and to provide sufficient depth to clear and thus not to contact the already finished convex surface of radius $R_2$; the pocket (36) cavity is an excellent receptor for mounting wax to fixedly support the blank (30′) for concave-surface finishing. As shown, an annular rib 37 rises locally out of the generally spherical support surface of radius $R_4$, to accurately nest all regions of integral haptic connection to the lens blank 30′, haptic features 31 being wax-fixed to surrounding concave spherical surface regions, as will be understood.

FIG. 16 additionally shows a master grinding element 38 in offset relation to the concave surface to be ground to radius $R_1$ on the posterior face of lens blank 30′. The master-grinding surface is to the desired radius $R_2$. And the resulting product, after release of the mounting wax, is as depicted in FIG. 5, except that sectioning should be for glass.

It will be understood that in a manner analogous to that described in connection with FIG. 14, the support 35 of FIG. 16 may provide for multiple support of severably connected blanks 30′. It will also be understood that support 35 lends itself to concave lens-surface grinding, regardless of the curvature or not of the anterior surface of the lens blank or blanks involved.

It will be understood that described processes and structures meet the above-stated objects, and that they are applicable in the context of a variety of materials and finishing techniques. For example, as to plastics, suitable single-sheet starting material 12 may be selected from available polyimides and polyamides, as well as porous polymethylmethacrilate (HEMA), polyethersulfone, polysulfone, polymethylmethacrilate (PMMA), polyesters, silicones, and polyethyltoluene (PET). Also by way of example, conventional techniques may be employed to build astigmatism-corrective curvatures and axial orientation into the integral haptic and lens structure, complete with a recognition profile or the like from which correct astigmatic-correction axis orientation can be recognized by the physician prescribing and/or installing the structure. Such orientation-refining techniques are described in my copending application Ser. No. 225,349 (filed Jan. 15, 1981), and in FIG. 17, I show an integrally formed lens 40 and haptic 41 wherein a small asymmetrical fillet 42 provides the means of recognizing correct orientation to achieve proper use of the astigmatism-correcting lens prescribed for the particular user.

Figure 17:
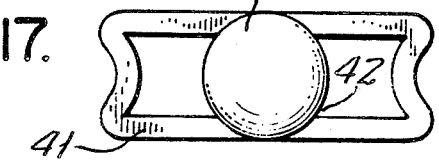
FIG. 17 is a plan view of a modified integral lens and haptic construction.
Figure 18:
FIG. 18 is a view in side elevation of a construction as in FIG. 17.

FIG. 18 illustrates that for any of the haptic configurations contemplated herein, and specifically in the context of the haptic configuration of FIG. 17, the deformation step used to create lens curvature may also be used to impart a haptic curvature generally in accordance with the curvature of the cornea. As noted from FIG. 18, this curvature is generally away from the originally flat nature of the starting sheet of material, but is generally tangent to the plane of the starting sheet in the vicinity of haptic juncture with the central lens element.

The reference to etching herein is to be understood as contemplating any of various well recognized selective erosion techniques. For the case of plastic erosion, these techniques include plasma etching, ion milling, and chemical etching. For the case of glass erosion, these techniques include hydrofluoric-acid etching and hydrofluoric-gaseous etching.

While the invention has been described in detail for various illustrative forms and processes, it will be understood that modifications may be made without departing from the scope of the invention.

For example, in either of the techniques illustrated by FIGS. 10 and 11, the severable tie elements 25-26-27 (25'-26') may be characterized by a central "pin-hole" opening external to the perimeter of each of the haptics thereby connected. Such pin-hole opening is illustratively shown at 27' in FIG. 10 and will be understood, in context with other such pin-hole openings (i.e., at other severable connections) to provide a precise optically scannable reference, as when automatically positioning a severably connected array of etched lens blanks with haptics, the positioning being for accurate placement in a multiple-lens press, and/or for precise automated laser cut-off of completed lens-haptic units 10-11 from the array.

Also, in connection with the pressing of lens elements as described above, it will be understood that the die used for pressing may be configured to develop in the lens a rounded outer edge, rather than the sharply defined outer edge shown for example at the circular peripheral edge of the convex surface of lens 10 in FIG. 5. A sharp exposed corner is thereby avoided.

Further, it will be understood that the lens-pressing operations described are purely illustrative, in that not only may astigmatism-corrective curvature be embodied in the pressing die, but so also may other complex curvatures, as for example the curvatures which will embody multifocal (e.g., bi-focal, tri-focal) properties in the single piece of press-formed lens-blank material.

What is claimed is:

1. A unitary contact lens and haptic construction removably applicable to a corneal surface and integrally formed from the same single sheet of transparent material, comprising a relatively thick rigid central lens component having a generally circular periphery, and a relatively thin pliant generally annular outer haptic component comprising plural leg formations radiating from the lens periphery at angular offset from each other, said haptic component being normally flat but so thin and of such axially compliant nature as to be self-conforming to the curvature of the cornea and to adhere thereto via surface moisture on the cornea.

2. The construction of claim 1, wherein the lens-component diameter is in the range of 5 to 8 mm.

3. The construction of claim 1, wherein the haptic-component thickness is in the order of one thousandth of an inch.

4. The construction of claim 1, wherein one surface of the haptic component is substantially flush with the corresponding surface of the lens component.

5. The construction of claim 1, wherein both surfaces of the haptic component are axially inwardly offset from both surfaces of the lens component.

6. The construction of claim 1, wherein said construction is one of plurality of like constructions in laterally offset relation and formed from the same single plastic sheet, being integrally but severably joined to each other at local proximity of their respective haptic components.

7. The construction of claim 6, wherein a short integrally formed tie between adjacent haptic components is the means of severable connection.

8. The construction of claim 1, wherein the pattern of haptic formations includes an observable asymmetric indicium which establishes a recognizable reference orientation, and wherein the central lens component includes an astigmatic-correction curvature having an axis orientation of predetermined angular orientation with respect to said reference orientation.

9. The construction of claim 1, in which said single sheet is initially flat and deformed into bowed curvature away from the initial flat of said sheet, the arc of the bow being substantially tangent to the initial flat of said sheet of haptic juncture with the lens component.

10. A unitary lens and haptic construction integrally formed from the same single sheet of transparent material, comprising a relatively thick rigid central lens component having a generally circular periphery, and a relatively thin pliant generally annular outer haptic component comprising plural leg formations radiating from the lens periphery at angular offset from each other, said construction being one of plurality of like constructions in laterally offset relation and formed from the same single plastic sheet, adjacent haptic components being integrally but severably joined to each other by a short integrally formed tie between adjacent haptic components, there being a locating aperture which characterizes a region of said tie external to the peripheral contour of each of the adjacent haptics thereby severably joined, whereby lens blanks associated with the severably connected haptics may be accurately positioned via such apertures, as for die-pressing alignment and orientation, and for cut-off.

11. A unitary contact lens and haptic construction removably applicable to a corneal surface and integrally formed from the same single sheet of transparent material, comprising a relatively rigid central lens component having a generally circular periphery, and a substantially fenestrated relatively pliant generally annular outer haptic component, said haptic component being normally flat but so thin and of such axially compliant nature as to be self-conforming to the curvature of the cornea and to adhere thereto via surface moisture on the cornea.

* * * * *